United States Patent [19]

Otake et al.

[11] Patent Number: 4,649,135

[45] Date of Patent: Mar. 10, 1987

[54] MYCOTRIENIN-RELATED COMPOUNDS

[75] Inventors: Noboru Otake, Yokohama; Haruo Seto, Hachioji; Tetsuo Sasaki, Kounosu; Masanori Sugita, Sakado; Shigeru Hiramoto, Kawagoe, all of Japan

[73] Assignee: Nisshin Flour Milling Co., Ltd., Japan

[21] Appl. No.: 852,441

[22] Filed: Apr. 15, 1986

[30] Foreign Application Priority Data

Apr. 22, 1985 [JP]  Japan .................................. 60-84615
Feb. 28, 1986 [JP]  Japan .................................. 61-41839

[51] Int. Cl.$^4$ .................... C07D 225/06; C12P 17/10; A61K 31/395

[52] U.S. Cl. .................................... 514/183; 435/121; 540/461

[58] Field of Search .......................... 540/461; 514/183

[56] References Cited

U.S. PATENT DOCUMENTS 4,521,339  6/1985  Otake et al. .......................... 540/461

Primary Examiner—Robert T. Bond
Attorney, Agent, or Firm—Abelman Frayne Rezac & Schwab

[57] ABSTRACT

Mycotrienin-related compounds called the T-23-X, -XI, -XII, -XIII and -XIV. These compounds are isolated and characterized by structural formula and other identifying data. They are useful in the treatment of tumors.

12 Claims, 10 Drawing Figures

MYCOTRIENIN-RELATED COMPOUNDS

FIELD OF THE INVENTION

This invention relates to mycotrienin-related compounds having new chemical structures. More particularly, the invention relates to new compounds called T-23-X, T-23-XI, T-23-XII, T-23-XIII and T-23-XIV which are expected for use in medicines because of their anti-tumor activities.

BACKGROUND OF THE INVENTION

We were successful in ascertaining the presence of the compounds of the following structural formulas with ansamycin skeleton having anti-tumor activities in the fermentation product of a new strain *Streptomyces rishiensis* T-23 (deposited at "Fermentation Research Institute, Agency of Industrial Science & Technology, MITI (Japan)" under the deposit No. FERM P-6141),

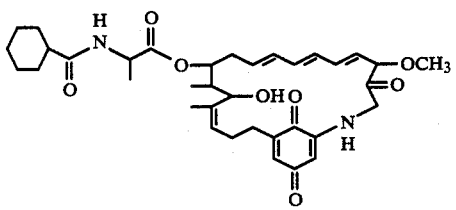

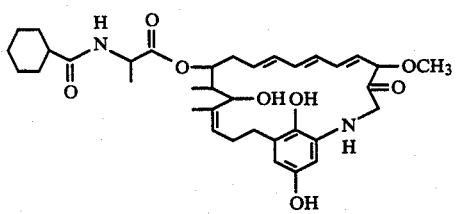

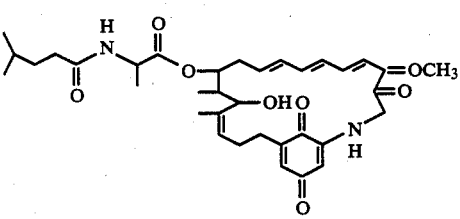

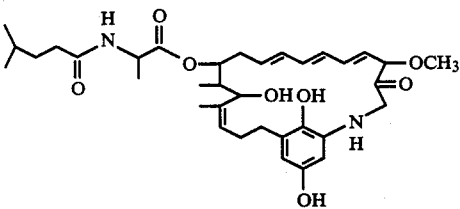

The above-mentioned compounds were then named in that order compound T-23-I, compound T-23-II, compound T-23-VIII and compound T-23-IX, respectively. The compounds T-23-I and -II were filed on Nov. 24, 1982 as U.S. Ser. No. 444,474 and issued on June 4, 1985 as U.S. Pat. No. 4,521,339, and the processes for the preparation thereof was filed on Jan. 29, 1985 as U.S. Ser. No. 696,040 which is a division of U.S. Ser. No. 444,474. Further, the compounds T-23-VIII and -IX were filed on Sept. 6, 1985 as U.S. Ser. No. 773,445.

According to our previous findings, the compounds T-23-I, -II, -VIII and -IX are prepared in the following manner.

More particularly, *Streptomyces rishiensis* T-23 strain mentioned above is cultured according to the conventional method for the culture of Actinomyces strain. The culture broth obtained in then divided into mycelia and a supernatant. An active fraction is extracted with acetone-water from the mycelia. The extract containing the active fraction is passed through a nonionic exchange resin to effect absorption of the active fraction thereon, followed by extraction with a solvent such as acetone or a lower alcohol. Separately, the active fraction is also extracted with an organic solvent directly from the supernatant. The two extracts are combined, and the organic solvent is removed from the mixture to give an aqueous phase which is then extracted with a water-immiscible solvent such as chloroform or ethyl acetate and then concentrated. Thereafter, the concentrate is charged with an aliphatic hydrocarbon solvent to precipitate the active fraction which is then adsorbed onto a silica gel column. After washing with benzene, the column is eluted with benzene-acetone (4:1) to obtain a T-23-I containing solution. The elution of the silica gel column is further continued with the same solvent to give a solution containing T-23-VIII. This column is further eluted with benzene-acetone (7:3) to obtain a T-23-II containing solution. After obtaining the T-23-II containing solution, the elution of the column with the same solvent is further continued, whereupon a T-23-IX containing solution is obtained.

SUMMARY OF THE INVENTION

As a result of further study, we have found the following facts. That is, the aforementioned active fraction which was precipitated with the aliphatic hydrocarbon solvent in a process for obtaining the solutions containing a series of T-23 substance including T-23-I is adsorbed onto a silica gel column. After washing with chloroform, the column is eluted with chloroform-methanol (100:1), and the eluate is fractionated in separate portions of a definite volume. Each of the fractions is subjected to silica gel thin layer chromatography developed with dichloromethane/methanol (15/1), whereupon a slight amount of active component ($R_f=0.50$) different from the compounds T-23-I ($R_f=0.64$) and T-23-VIII ($R_f=0.63$) is confirmed to be present in the fraction obtained after elution of the fraction containing the above-mentioned T-23-I and T-23-VIII, a slight amount of active component ($R_f=0.32$) different from the above-mentioned slight amount of active component ($R_f=0.50$) is confirmed to be present in the fraction obtained after elution of the fraction containing the above-mentioned slight amount of active component ($R_f=0.50$) and, furthermore, three kinds of slight amounts of active components ($R_f=0.31$, $R_f=0.30$ and $R_f=0.29$) different from the above-mentioned two kinds of slight amounts of active components ($R_f=0.50$ and $R_f=0.32$) are confirmed to be present in the fraction obtained after elution of the fractions containing the above-mentioned two kinds of slight amounts of active components ($R_f=0.50$ and $R_f=0.32$), respectively, in that order, and the compounds T-23-II ($R_f=0.28$) and T-23-IX ($R_f=0.27$) are then eluted after elution of the above-mentioned three kinds of slight amounts of active components.

Thereupon, we have called the component of $R_f=0.32$ as component T-23-X, the component of $R_f=0.50$ as compound T-23-XI, the component of $R_f=0.31$ as compound T-23-XII, the component of $R_f=0.30$ as compound T-23-XIII, and the component of $R_f=0.29$ as compound T-23-XIV. On study of physicochemical properties of these compounds, we have confirmed that they are new compounds represented respectively by the undermentioned structural formulas and possess anti-tumor activities. The present invention thus has been accomplished on the basis of the facts found above.

In accordance with the present invention, there are provided compounds which are identified by the following structural formulas, respectively.

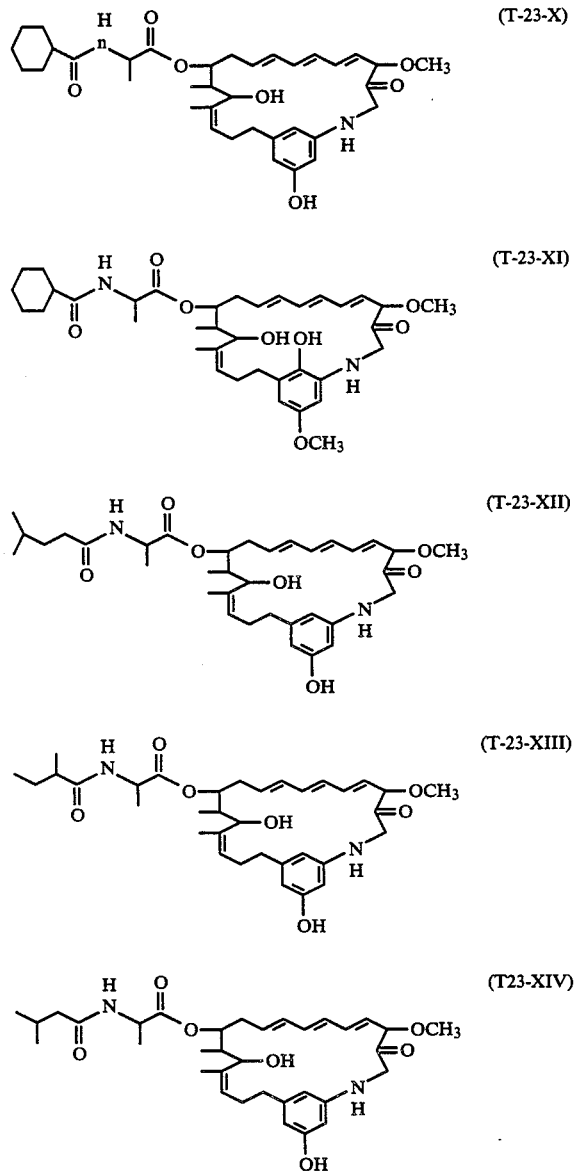

For convenience, the above-mentioned compounds T-23-X, -XII, -XIII and -XIV can be generically represented by the following structural formula

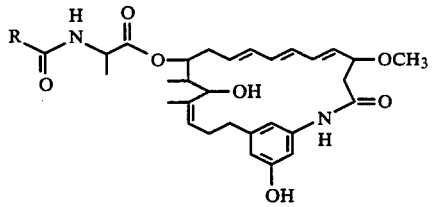

wherein R represents isobutyl, sec.-butyl, isopentyl or cyclohexyl.

BRIEF DISCLOSURE OF THE DRAWINGS

DETAILED DISCLOSURE OF THE INVENTION

According to the invention, the fractions containing T-23-X, T-23-XI, T-23-XII, T-23-XIII and T-23-XIV are concentrated under reduced pressure, and thereafter the concentrate is subjected to preparative silica gel thin layer chromatography developed with dichloromethane/methanol (15:1), whereupon compound T-23-XI appears at $R_f=0.50$, compound T-23-X at $R_f=0.32$, compound T-23-XII at $R_f=0.31$, compound T-23-XIII at $R_f=0.30$ and compound T-23-XIV at $R_f=0.29$. The fractions corresponding to their respective compounds are individually scraped out and then eluted with a mixed solvent of chloroform/methanol (10/1). The eluates are concentrated individually in vacuo to obtain the compounds T-23-X, T-23-XI, T-23-XII, T-23-XIII and T-23-XIV, respectively as white powder.

Alternatively, the above-mentioned T-23-X, T-23-XII, T-23-XIII and T-23-XIV containing fraction is concentrated in vacuo. The concentrate is then dissolved in a small amount of chloroform, and the solution was subjected to preparative high performance liquid chromatography using a silica gel column whereby elution of the column is carried out with a solvent of chloroform/methanol (30:1) at a flow rate of 5 ml/min. The eluate is detected by means of UV absorption at 270 nm, whereupon three peaks appear at the retention time of 19, 21 and 22 minutes, respectively, after appearance at the 18-minutes retention time of a peak corresponding to compound T-23-X. Concentration in vacuo of the eluates corresponding to these three peaks gives the compounds T-23-XII, T-23-XIII and T-23-XIV, respectively, as white powder.

These compounds T-23-X, T-23-XI, T-23-XII, T-23-XIII and T-23-XIV have been confirmed, similarly to the aforementioned compounds T-23-I, T-23-II, etc., to be of anti-tumor activities, and hence are expected to be used for medicine.

The compounds T-23-X, T-23-XI, T-23-XII, T-23-XIII and T-23-XIV of the present invention may be prepared by the processes as mentioned above. Study of these compounds on the physicochemical properties and biological activities revealed that they were of the characteristics as listed below.

(A) Compound T-23-X
1. Appearance: Colorless amorphous powder
2. M.W.: 622
3. Elementary analysis:

|  | C % | H % | N % | O % |
|---|---|---|---|---|
| Calc. for $C_{36}H_{50}N_2O_7$: | 69.43 | 8.09 | 4.50 | 17.98 |
| Found: | 69.20 | 8.23 | 4.48 | 18.09 |

Figure 1:
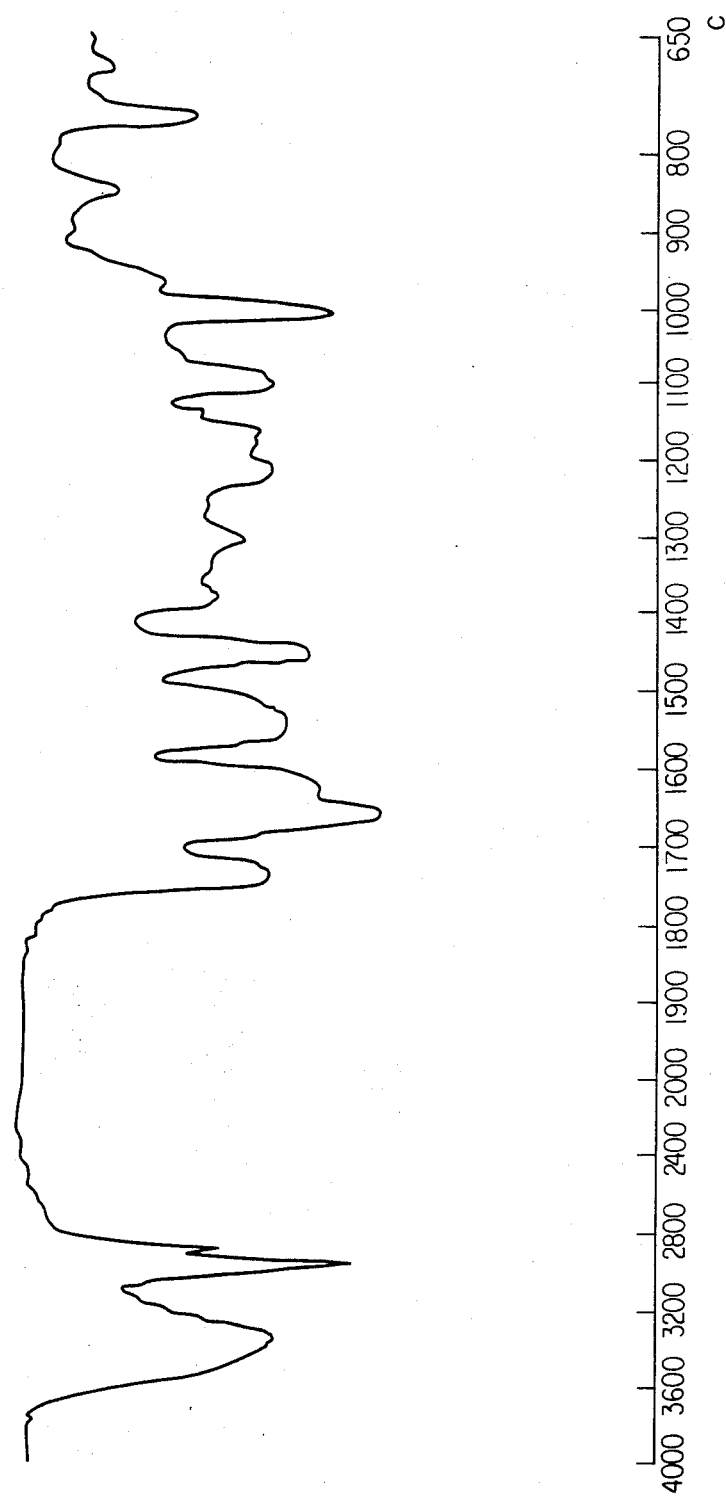
FIG. 1 is IR absorption spectrum of compound T-23-X.

4. $[\alpha]_D^{27} = +151°$ (C=0.169, MeOH)
5. m.p. 135°
6. UV absorption spectrum (in methanol)
$\lambda_{max}$ 256 nm ($\epsilon$ 25500); 260 nm ($\epsilon$ 27000); 271 nm ($\epsilon$ 33000); 282 nm ($\epsilon$ 25400).
7. IR absorption spectrum (in KBr) (see FIG. 1)
$\nu_{max}$ 3350, 2950, 1730, 1650, 1540, 1450, 1380, 1300, 1210, 1100, 1000 cm$^{-1}$.
8. Solubility:
Soluble in methanol, ethanol, acetone, ethyl acetate, chloroform and pyridine,
Insoluble in n-hexane, petroleum ether and water
9. $^{13}$C—NMR spectrum chemical shift (in CDCl$_3$)

| No. | $\delta_c$* | No. | $\delta_c$* |
|---|---|---|---|
| 1 | 168.8 (s) | 15 | 124.8 (d) |
| 2 | 43.6 (t) | 16 | 25.6 (t) |
| 3 | 78.9 (d) | 17 | 33.2 (t) |
| 4 | 130.7 (d) | 18 | 144.0 (s) |
| 5 | 134.1 (d) | 19 | 112.2 (d) |
| 6 | 129.3 (d) | 20 | 138.4 (s) |
| 7 | 133.7 (d) | 21 | 105.9 (d) |
| 8 | 133.4 (d) | 22 | 157.3 (s) |
| 9 | 129.5 (d) | 23 | 111.0 (d) |
| 10 | 33.2 (t) | 24 | 9.9 (q) |
| 11 | 75.5 (d) | 25 | 20.4 (q) |
| 12 | 39.4 (d) | 26 | 56.7 (q) |
| 13 | 68.4 (d) | 27 | 172.9 (s) |
| 14 | 138.2 (s) | 28 | 48.6 (d) |
| 29 | 17.6 (q) | 33 | 25.6 (t) |
| 30 | 176.7 (s) | 34 | 25.6 (t) |
| 31 | 44.9 (d) | 35 | 25.6 (t) |
| 32 | 29.4 (t) | 36 | 29.4 (t) |

*Multiplicity in off-resonance spectrum

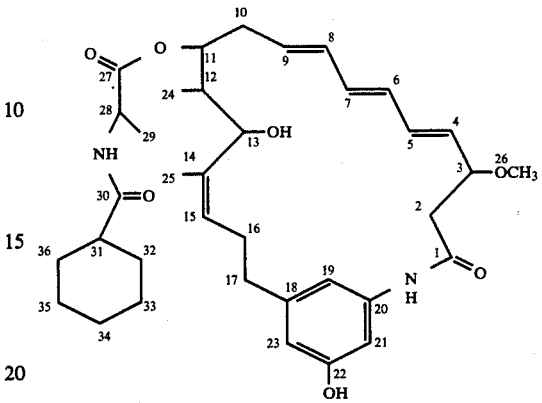

Figure 2:
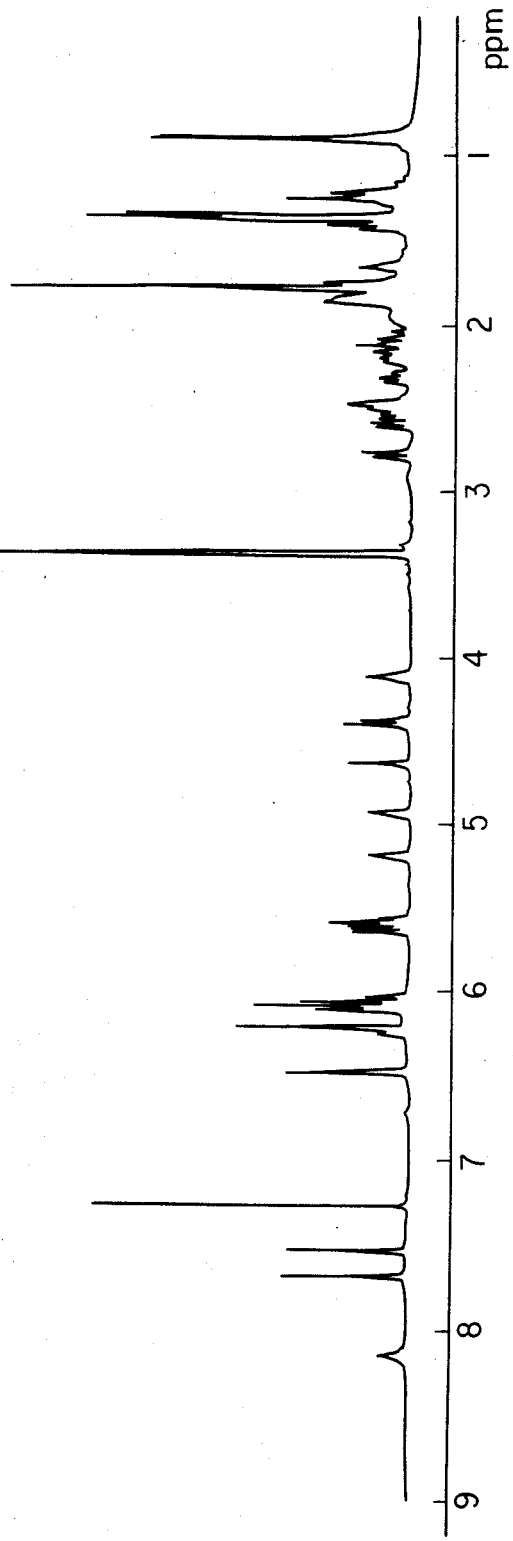
FIG. 2 is $^1$H—NMR spectrum of compound T-23-X.

10. $^1$H—NMR spectrum (in CDCl$_3$) (see FIG. 2)

(B) Compound T-23-XI
1. Appearance: colorless amorphous powder
2. M.W.: 652
3. Elementary analysis

|  | C % | H % | N % | O % |
|---|---|---|---|---|
| Calc. for $C_{37}H_{52}N_2O_8$: | 68.07 | 8.03 | 4.29 | 19.61 |
| Found: | 68.04 | 8.07 | 4.26 | 19.63 |

Figure 3:
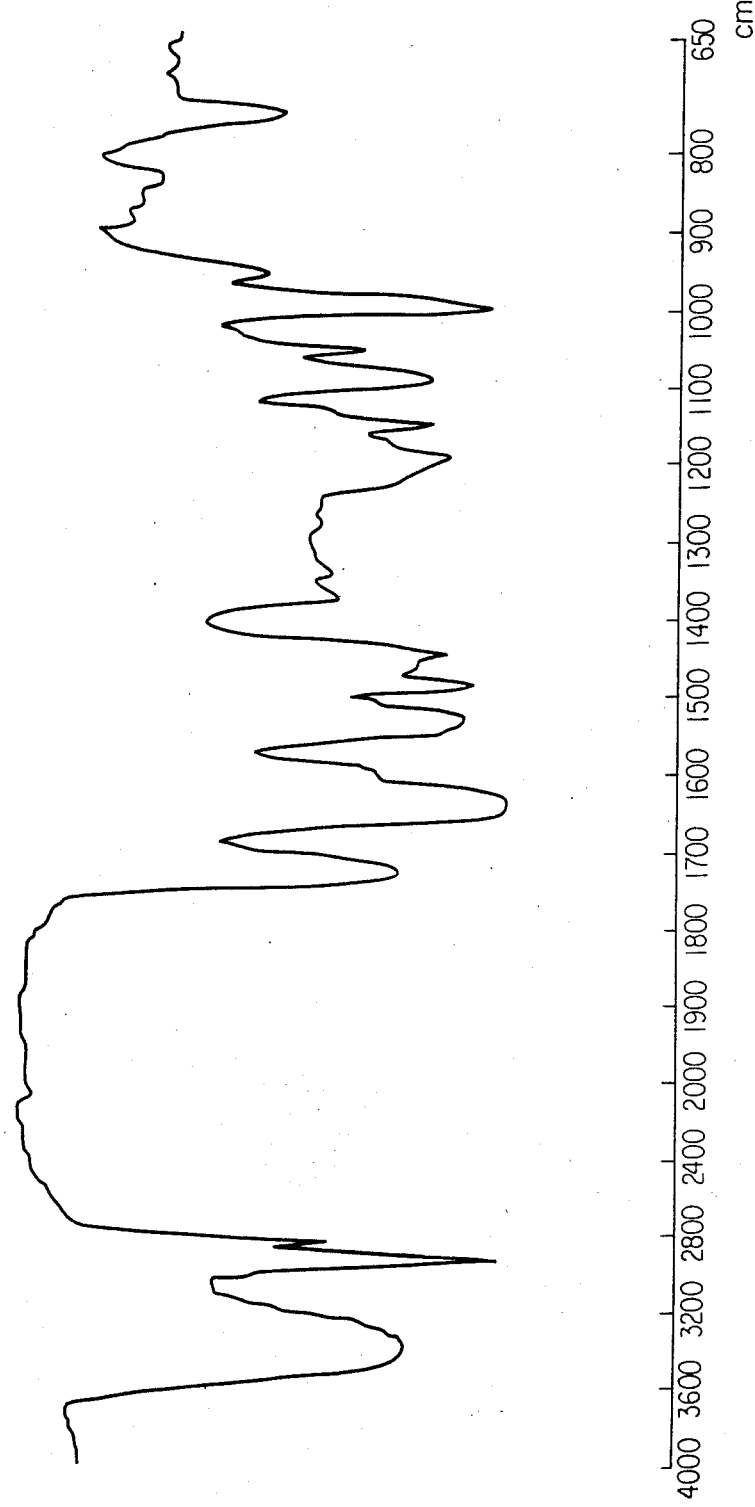
FIG. 3 is IR absorption spectrum of compound T-23-XI.

4. $[\alpha]_D^{25} = +373°$ (C=0.045, MeOH)
5. m.p. 128° C.
6. UV absorption spectrum (in CH$_3$OH)
$\lambda_{max}$ 262 nm ($\epsilon$ 44100); 272 nm ($\epsilon$ 57600); 281 nm ($\epsilon$ 43700).
7. IR absorption spectrum (in KBr) (see FIG. 3)
$\nu_{max}$ 3350, 2930, 1730, 1640, 1530, 1480, 1450, 1380, 1200, 1100, 1000 cm$^{-1}$.
8. Solubility:
Soluble in methanol, ethanol, acetone, ethyl acetate, chloroform and pyridine
Insoluble in n-hexane, petroleum ether and water
9. $^{13}$C—NMR spectrum chemical shift (in CDCl$_3$)

| No. | $\delta_c$* | No. | $\delta_c$* |
|---|---|---|---|
| 1 | 169.7 (s) | 19 | 142.2 (s) |
| 2 | 43.0 (t) | 20 | 125.0 (s) |
| 3 | 79.1 (d) | 21 | 106.0 (d) |
| 4 | 129.4 (d) | 22 | 152.5 (s) |
| 5 | 134.6 (d) | 23 | 115.1 (d) |
| 6 | 129.2 (d) | 24 | 9.6 (q) |
| 7 | 134.4 (d) | 25 | 20.2 (q) |
| 8 | 133.6 (d) | 26 | 56.6 (q) |
| 9 | 129.3 (d) | 27 | 173.1 (q) |
| 10 | 33.8 (t) | 28 | 48.5 (d) |
| 11 | 75.3 (d) | 29 | 17.8 (q) |
| 12 | 38.9 (d) | 30 | 176.4 (s) |
| 13 | 68.4 (d) | 31 | 45.1 (d) |
| 14 | 138.0 (s) | 32 | 29.4 (t) |
| 15 | 124.2 (d) | 33 | 25.6 (t) |
| 16 | 26.5 (t) | 34 | 25.6 (t) |
| 17 | 32.2 (t) | 35 | 25.6 (t) |

-continued

| No. | $\delta_c$* | No. | $\delta_c$* |
|---|---|---|---|
| 18 | 133.2 (s) | 36 | 29.4 (t) |

*Multiplicity in off-resonance spectrum

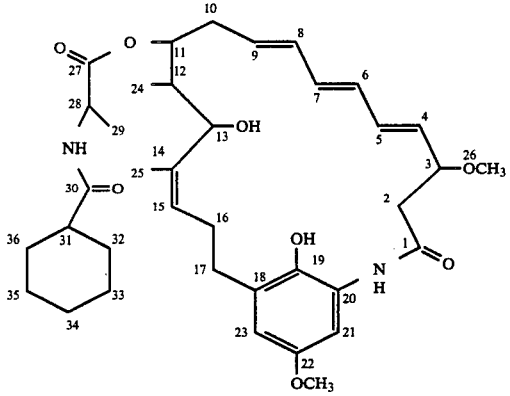

Figure 4:
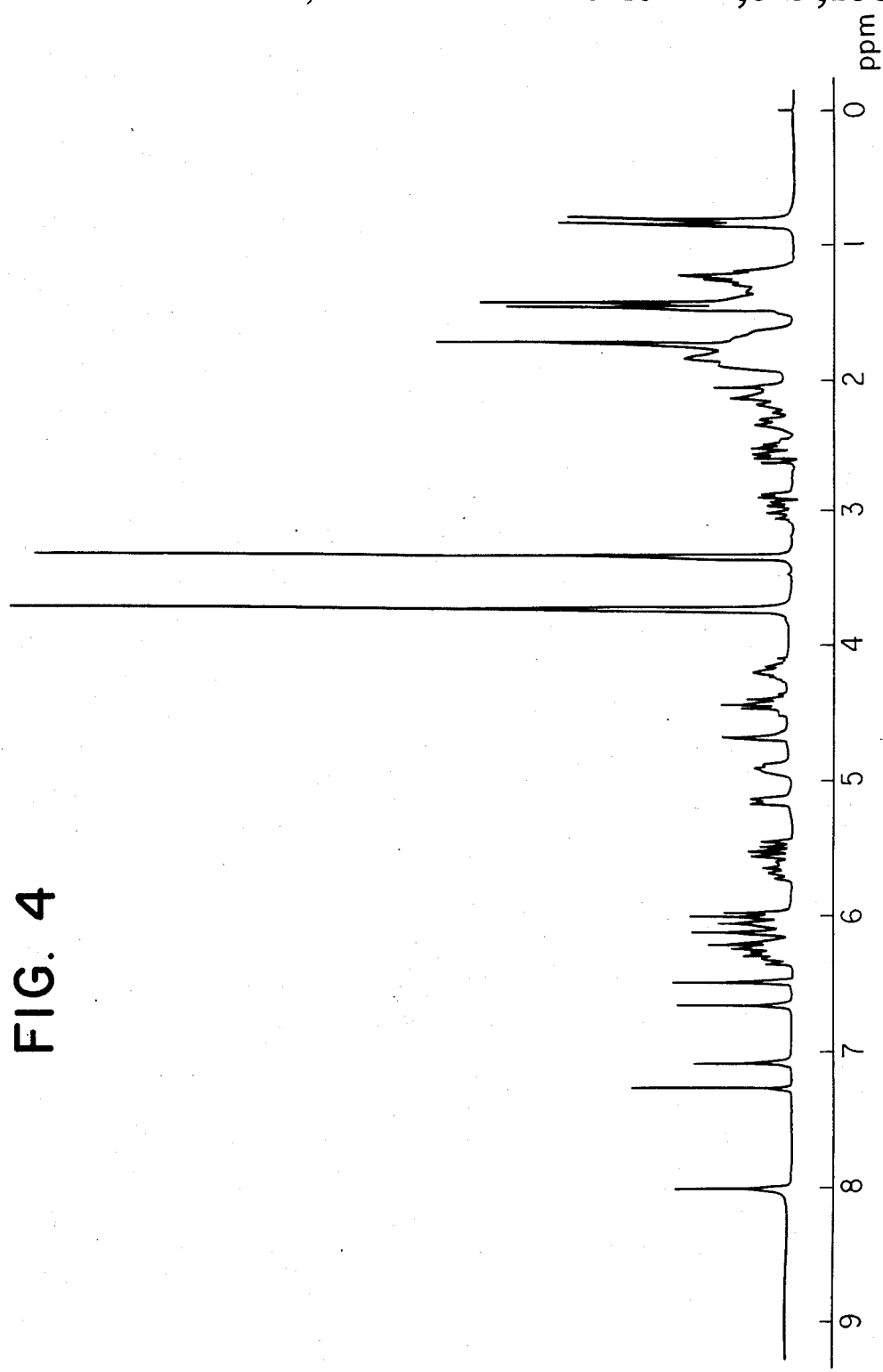
FIG. 4 is $^1$H—NMR spectrum of compound T-23-XI.

10. $^1$H—NMR spectrum (in CDCl$_3$) (see FIG. 4)

(C) Biological activity

The compounds T-23-X and T-23-XI are compared with the compound T-23-II with regard to anti-tumor activity (in vitro) against L-5178Y tumor cells.

| T-23-X | | T-23-XI | | T-23-II | |
|---|---|---|---|---|---|
| Conc. (μg/ml) | State of cell growth | Conc. (μg/ml) | State of cell growth | Conc. (μg/ml) | State of cell growth |
| 1 | — | 1 | — | 0.4 | — |
| 0.33 | — | 0.33 | — | 0.2 | + |
| 0.11 | — | 0.11 | — | 0.1 | + |
| 0.04 | + | 0.04 | + | 0.05 | + |

+ cell growth
− no cell growth

The cell growth was observed by a dilution method using an Eagle-NEM medium (Nissui) supplemented with 10% horse serum and 100 mg/l asparagine and cultivated at 37° C. for 120 hours. The test compounds in ethanol solution were added to an assay system.

The above data show that both compounds T-23-X and T-23-XI are expected to be of strong carcinostatic effect because they exhibit no growth of tumor cells at about ⅓ of minimum inhibitory concentration as compared with compound T-23-II. More particularly, compound T-23-II shows no growth of tumor cells at 0.4 μg/ml, whereas compounds T-23-X and -XI show no growth of tumor cells at 0.11 μg/ml.

(D) Compound T-23-XII
1. Appearance: colorless amorphous powder
2. M.W.: 610
3. Elementary analysis

| | C % | H % | N % | O % |
|---|---|---|---|---|
| Calc. for C$_{35}$H$_{50}$N$_2$O$_7$: | 68.83 | 8.25 | 4.59 | 18.33 |
| Found: | 68.69 | 8.35 | 4.57 | 18.39 |

Figure 5:
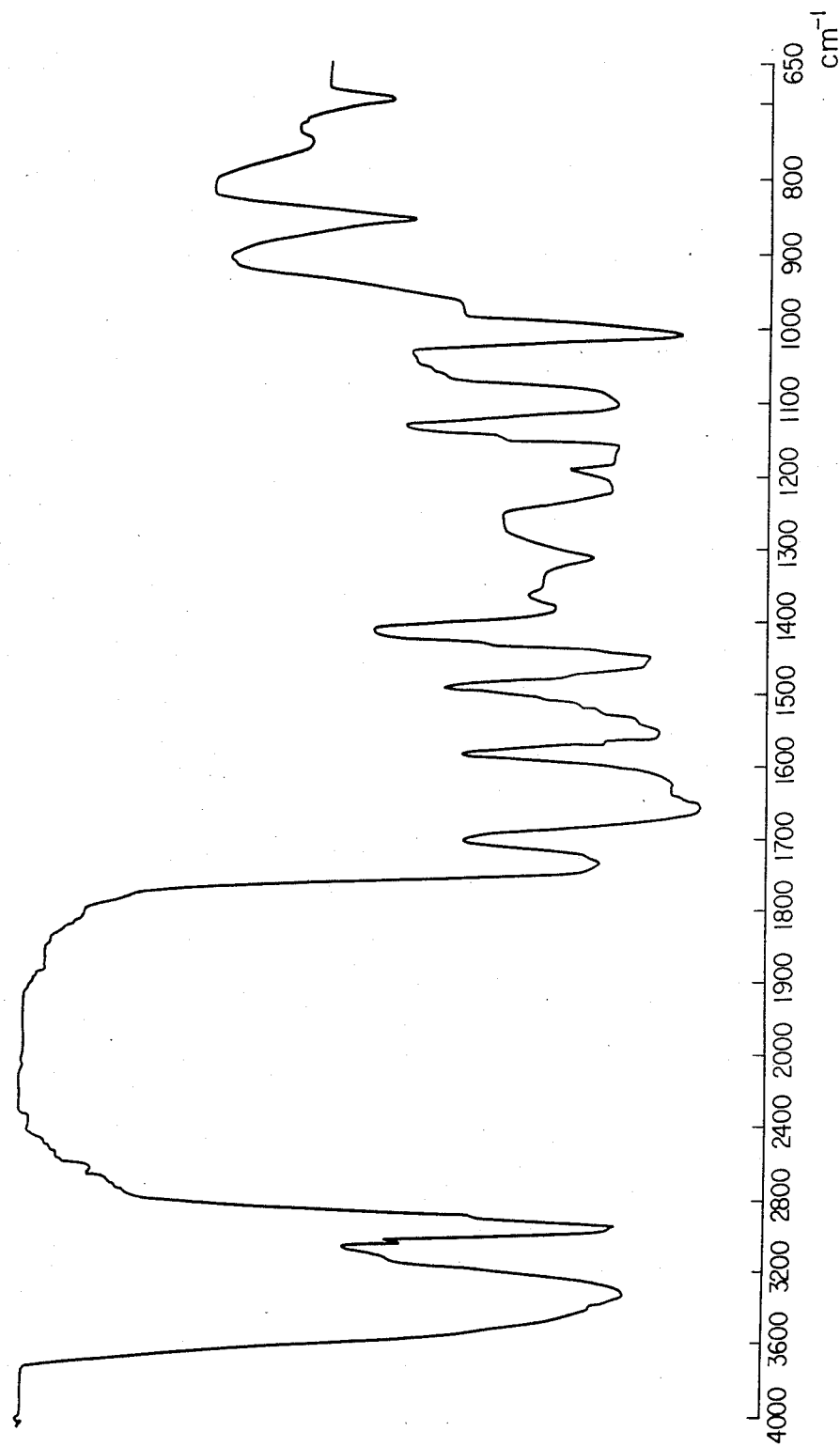
FIG. 5 is IR absorption spectrum of compound T-23-XII.

4. $[\alpha]_D^{25} = +187°$ (C=0.062, MeOH)
5. m.p. 105° C.
6. UV absorption spectrum (in CH$_3$OH)
   $\lambda_{max}$ 250 nm (ε 31100); 259 nm (ε 33100); 271 nm (ε 40700); 282 nm (ε 31400).
7. IR absorption spectrum (in KBr) (see FIG. 5)

$\nu_{max}$ 3300, 2940, 1740, 1660, 1550, 1450, 1380, 1310, 1220, 1100, 1000 cm$^{-1}$.

8. Solubility:
   Soluble in methanol, ethanol, acetone, ethyl acetate, chloroform and pyridine,
   Insoluble in n-hexane, petroleum ether and water
9. $^{13}$C—NMR spectrum chemical shift (in CDCl$_3$)

| No. | $\delta_c$* | No. | $\delta_c$* |
|---|---|---|---|
| 0-1 | 168.7 (s) | 0-18 | 144.0 (s) |
| -2 | 43.5 (t) | -19 | 112.0 (d) |
| -3 | 78.6 (d) | -20 | 138.5 (s) |
| -4 | 130.6 (d) | -21 | 105.8 (d) |
| -5 | 134.1 (d) | -22 | 157.2 (s) |
| -6 | 129.4 (d) | -23 | 110.8 (d) |
| -7 | 133.6 (d) | -24 | 9.9 (q) |
| -8 | 133.4 (d) | -25 | 20.4 (q) |
| -9 | 129.3 (d) | -26 | 56.8 (q) |
| -10 | 33.2 (t) | -27 | 172.9 (s) |
| -11 | 75.4 (d) | -28 | 48.7 (d) |
| -12 | 39.5 (d) | -29 | 17.7 (q) |
| -13 | 68.4 (d) | -30 | 173.9 (s) |
| -14 | 138.2 (s) | -31 | 34.3 (t) |
| -15 | 124.8 (d) | -32 | 34.3 (t) |
| -16 | 29.5 (t) | -33 | 27.8 (d) |
| -17 | 36.2 (t) | -34 | 22.3 (q) |
| | | -35 | 22.3 (q) |

*Multiplicity in off-resonance spectrum

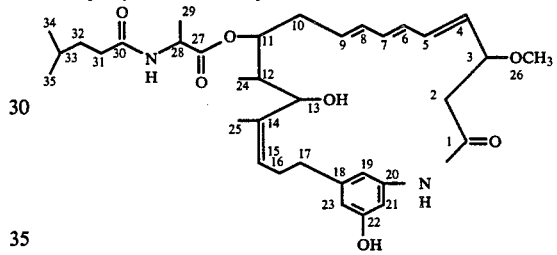

Figure 6:
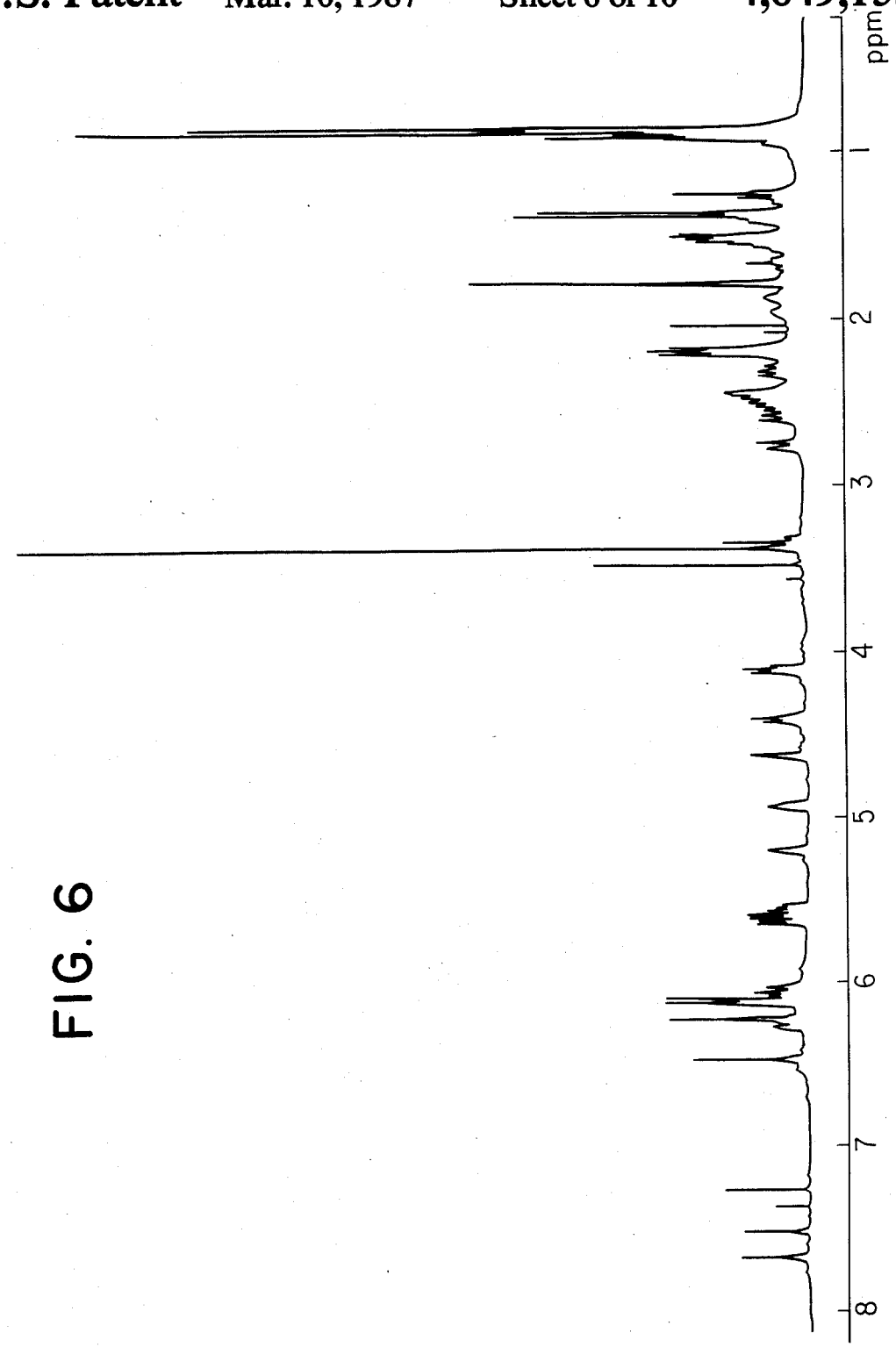
FIG. 6 is $^1$H—NMR spectrum of compound T-23-XII.

10. $^1$H—NMR spectrum (in CDCl$_3$) (see FIG. 6)

(E) Compound T-23-XIII
1. Appearance: colorless amorphous powder
2. M.W.: 596
3. Elementary analysis

| | C % | H % | N % | O % |
|---|---|---|---|---|
| Calc. for C$_{34}$H$_{48}$N$_2$O$_7$: | 68.43 | 8.11 | 4.69 | 18.77 |
| Found: | 68.21 | 8.06 | 4.68 | 19.05 |

Figure 7:
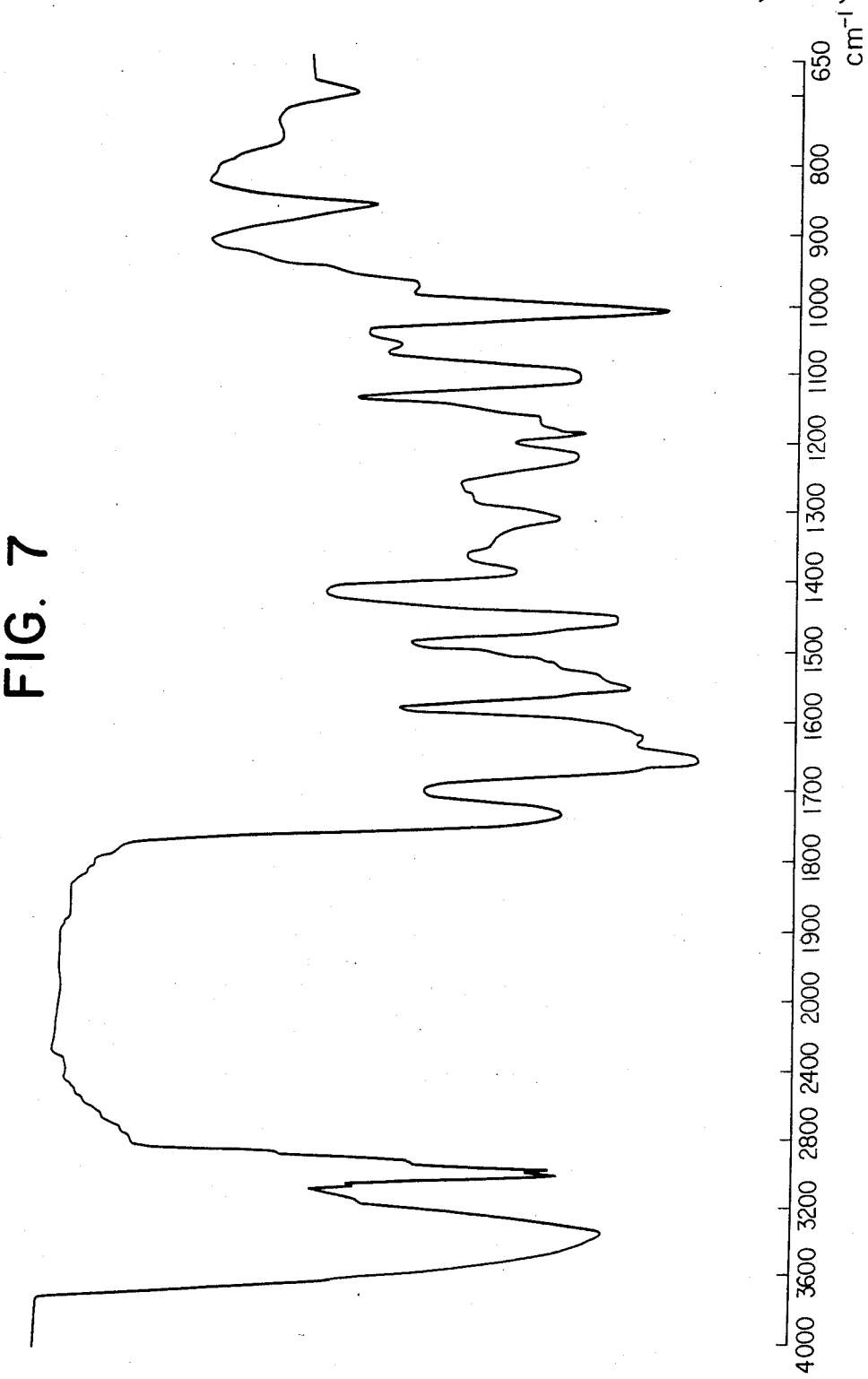
FIG. 7 is IR absorption spectrum of compound T-23-XIII.

4. $[\alpha]_D^{25} = +232°$ (C=0.034, MeOH)
5. m.p. 127° C.
6. UV absorption spectrum (in CH$_3$OH)
   $\lambda_{max}$ 250 nm (ε 31100); 260 nm (ε 32700); 271 nm (ε 39900); 282 nm (ε 30600).
7. IR absorption spectrum (in KBr) (see FIG. 7)
   $\nu_{max}$ 3300, 2940, 1740, 1670, 1560, 1460, 1390, 1320, 1220, 1100, 1020 cm$^{-1}$.
8. Solubility:
   Soluble in methanol, ethanol, acetone, ethyl acetate, chloroform and pyridine,
   Insoluble in n-hexane, petroleum ether and water
9. $^{13}$C—NMR spectrum chemical shift (in CDCl$_3$)

| No. | $\delta_c$* | No. | $\delta_c$* |
|---|---|---|---|
| 0-1 | 168.7 (s) | 0-18 | 144.0 (s) |
| -2 | 43.5 (t) | -19 | 112.0 (d) |
| -3 | 78.6 (d) | -20 | 138.4 (s) |
| -4 | 130.6 (d) | -21 | 105.8 (d) |
| -5 | 134.1 (d) | -22 | 157.2 (s) |
| -6 | 129.4 (d) | -23 | 110.8 (d) |

-continued

| No. | $\delta_c$* | No. | $\delta_c$* |
|---|---|---|---|
| -7 | 133.5 (d) | -24 | 9.8 (q) |
| -8 | 133.3 (d) | -25 | 20.3 (q) |
| -9 | 129.3 (d) | -26 | 56.7 (q) |
| -10 | 33.1 (t) | -27 | 172.8 (s) |
| -11 | 75.4 (d) | -28 | 48.5 (d) |
| -12 | 39.5 (d) | -29 | 17.8 (q) |
| -13 | 68.4 (d) | -30 | 177.0 (s) |
| -14 | 138.3 (s) | -31 | 42.8 (d) |
| -15 | 124.9 (d) | -32 | 27.2 (t) |
| -16 | 29.6 (t) | -33 | 11.8 (q) |
| -17 | 36.2 (t) | -34 | 17.1 (q) |

*Multiplicity in off-resonance spectrum

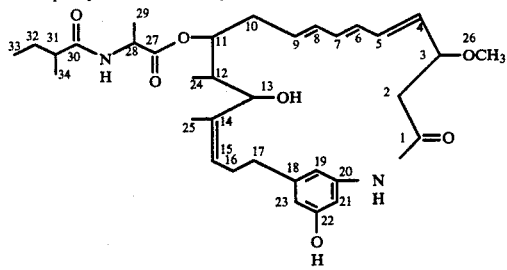

Figure 8:
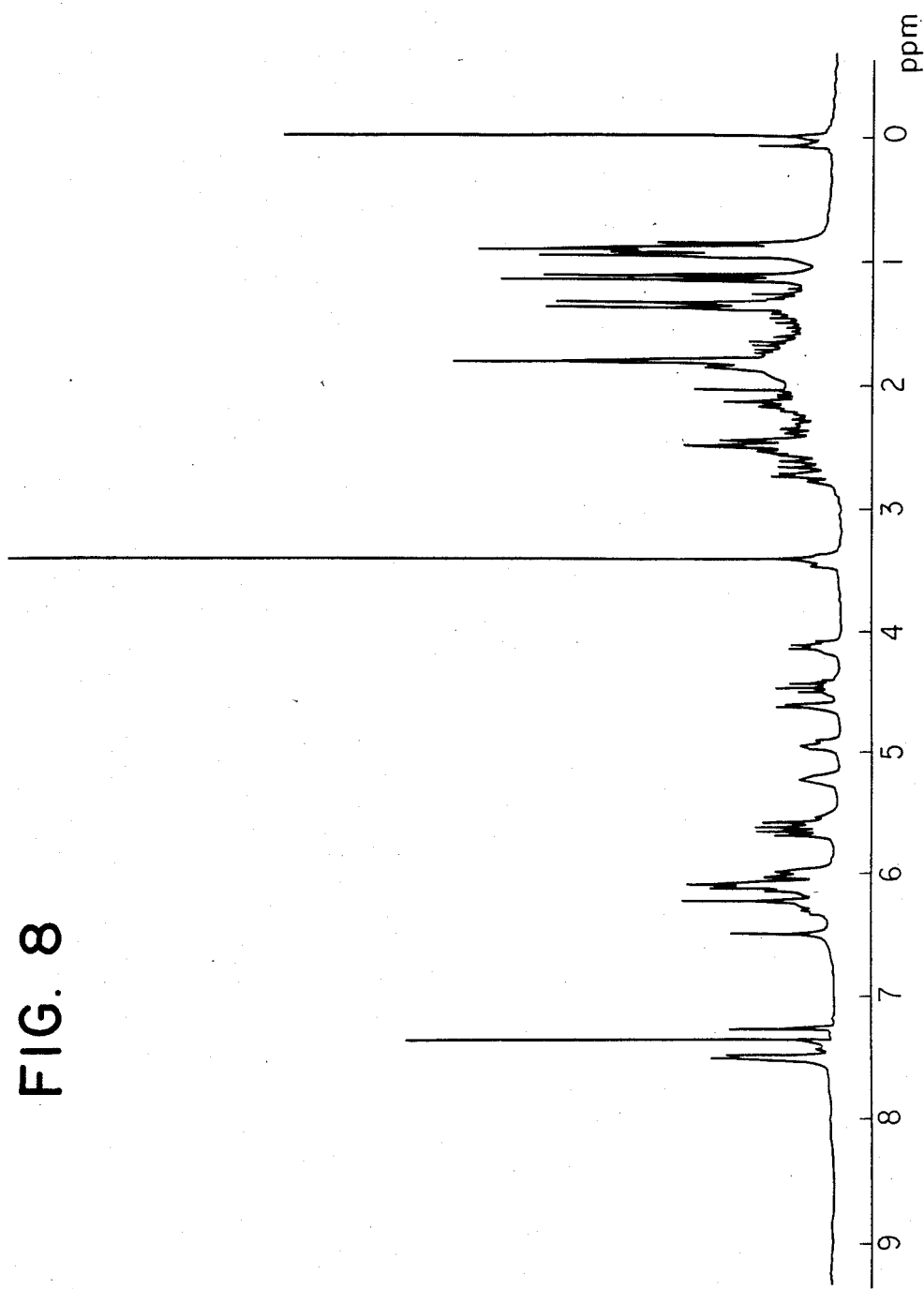
FIG. 8 is $^1$H—NMR spectrum of compound T-23-XIII.

10. $^1$H—NMR spectrum (in CDCl$_3$) (see FIG. 8)

(F) Compound T-23-XIV

1. Appearance: colorless amorphous powder
2. M.W.: 596
3. Elementary analysis

|  | C % | H % | N % | O % |
|---|---|---|---|---|
| Calc. for C$_{34}$H$_{48}$N$_2$O$_7$: | 68.43 | 8.11 | 4.69 | 18.77 |
| Found: | 68.29 | 8.30 | 4.67 | 18.74 |

4. $[\alpha]_D^{25} = +267°$ (C=0.015, MeOH).
5. m.p. 127° C.
6. UV absorption spectrum $\lambda_{max}$ 252 nm ($\epsilon$ 37600); 259 nm ($\epsilon$ 39700); 271 nm ($\epsilon$ 48700); 282 nm ($\epsilon$ 37500).

Figure 9:
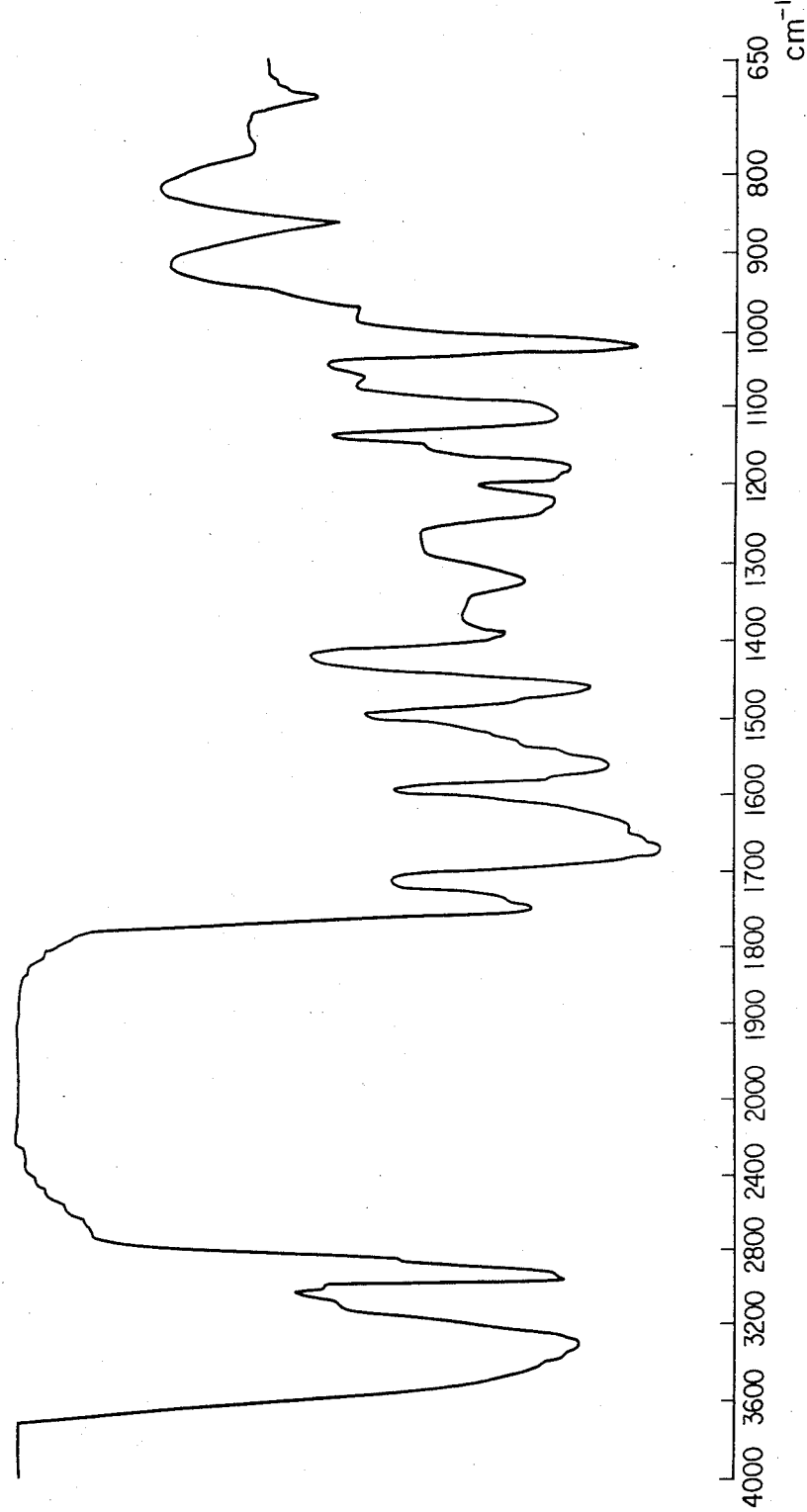
FIG. 9 is IR absorption spectrum of compound T-23-XIV.

7. IR absorption spectrum (in KBr) (see FIG. 9)

$\nu_{max}$ 3300, 2940, 1740, 1670, 1560, 1460, 1390, 1320, 1220, 1100, 1020 cm$^{-1}$.

8. Solubility:
   Soluble in methanol, ethanol, acetone, ethyl acetate, chloroform and pyridine,
   Insoluble in n-hexane, petroleum ether and water 9. $^{13}$C—NMR spectrum chemical shift (in CDCl$_3$)

| No. | $\delta_c$* | No. | $\delta_c$* |
|---|---|---|---|
| 0-1 | 168.7 (s) | 0-18 | 144.0 (s) |
| -2 | 43.5 (t) | -19 | 112.0 (d) |
| -3 | 78.6 (d) | -20 | 138.3 (s) |
| -4 | 130.6 (d) | -21 | 105.8 (q) |
| -5 | 134.1 (d) | -22 | 157.2 (s) |
| -6 | 129.4 (d) | -23 | 110.8 (d) |
| -7 | 133.5 (d) | -24 | 9.8 (q) |
| -8 | 133.3 (d) | -25 | 20.3 (q) |
| -9 | 129.3 (d) | -26 | 56.8 (q) |
| -10 | 33.2 (t) | -27 | 172.8 (s) |
| -11 | 75.4 (d) | -28 | 48.6 (d) |
| -12 | 39.6 (d) | -29 | 17.7 (q) |
| -13 | 68.4 (d) | -30 | 173.1 (s) |
| -14 | 138.5 (s) | -31 | 45.5 (t) |
| -15 | 124.8 (d) | -32 | 26.2 (d) |
| -16 | 29.6 (t) | -33 | 22.4 (q) |
| -17 | 36.2 (t) | -34 | 22.4 (q) |

*Multiplicity in off-resonance spectrum

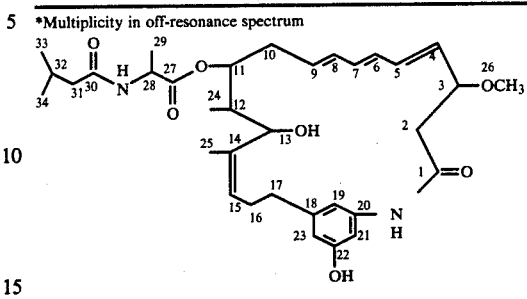

Figure 10:
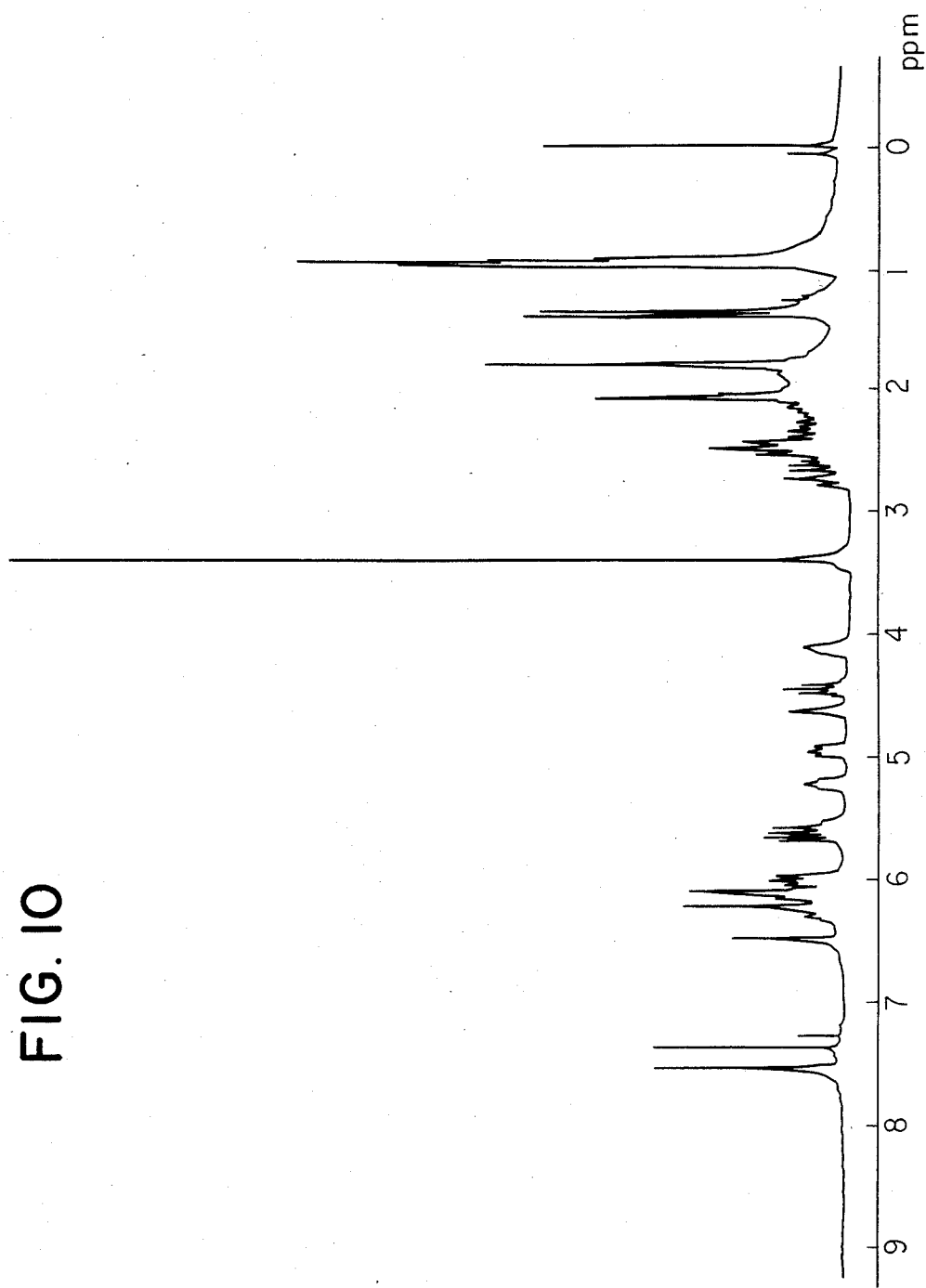
FIG. 10 is $^1$H—NMR spectrum of compound T-23-XIV.

10. $^1$H—NMR spectrum (in CDCl$_3$) (see FIG. 10)

(G) Biological activity:

The compounds T-23-XII, -XIII and -XIV of the present invention exhibit biological activities as shown in the table below and are expected for use in anti-tumor agents.

| Conc. ($\mu$g/ml) | Anti-tumor activity (in vitro) against L-5178Y tumor cells | | |
|---|---|---|---|
| | T-23-XII | State of cell growth T-23-XIII | T-23-XIV |
| 2.0 | — | — | — |
| 1.0 | — | — | — |
| 0.5 | — | — | — |
| 0.25 | — | — | — |
| 0.125 | — | + | + |
| 0.0625 | + | + | + |

+ cell growth
— no cell growth

The cell growth was observed by a dilution method using as Eagle-NEM medium (Nissui) supplemented with 10% horse serum and 100 mg/l asparagine and cultivated at 37° C. for 120 hours.

The following are the non-limitative examples to illustrate the present invention.

EXAMPLE 1

One loopful of strain T-23 of *Streptomyces rishiensis* preserved on a test tube slant medium comprising 1.0% soluble statch, 0.2% yeast extract and 1.5% agar was inoculated into a Sakaguchi flask containing 100 ml of seed medium comprising 1.0% soluble starch, 1.0% waste molasses, 1.0% meat extract and 1.0% polypeptone (pH 7.0). The flask was incubated on a reciprocal shaker at 30° C. for 48 hours. A 0.5 ml aliquot of the culture was inoculated into a Sakaguchi flask containing 100 ml of the same medium and the culture was incubated on a reciprocal shaker at 30° C. for 24 hours thereby to obtain a seed inoculum for the production culture using a jar fermenter.

For carrying out the production culture, there were used six 30 liter-capacity stainless steel jar fermenters each containing 15.0 liters of a medium (pH 7.0) containing 1.0% glucose, 1.5% soluble starch, 1.5% soya bean flour, 0.2% dried yeast, 0.2% ammonium sulfate, 0.5% NaCl, 0.4% precipitated calcium carbonate and 0.33% antifoaming agent (Toshiba "Silicone" YMA 6509). The inoculum obtained was added to each fermenter at the proportion of 4.0%, and cultivation with aeration and agitation (15.0/min., 200 r.p.m.) was carried out at 30° C. for 24 hours.

Immediately after completion of the cultivation, the mycelia were filtered off by means of a large type continuous centrifuge, soaked in 20 liters of 60% aqueous acetone solution with stirring for a short while and then allowed to stand for 3 hours. Then, the mycelia were filtered to obtain an extract. The same treatment was repeated twice. The extracts were combined to amount up to 40 liters. From the combined extracts, acetone was distilled off in vacuo to leave 18.0 liters of an aqueous solution. To this solution (18.0 liters) was added 6.5 kg sodium chloride, and the resulting solution was extracted twice with each 9.0 liters ethyl acetate. The ethyl acetate solution obtained was dried over $Na_2SO_4$ (1 kg) and allowed to stand for a while. After dehydration, the solution was concentrated in vacuo to an appropriate volume. To the concentrate obtained was added hexane, thereby to precipitate the fraction containing the active substances. The precipitate obtained was washed with hexane and then dried. The crude mixture obtained was dissolved in 150 ml of chloroform and adsorbed on a silica gel column (8 cm×40 cm), washed with chloroform and eluted with chloroform/methanol (100:1). The first 2.5 liters of the eluate were discarded because of its containing no active substance, and thereafter the eluates that follows were fractionated in each 15 ml portions. Each fraction was subjected to thin layer chromatography (developing solvent: dichloromethane/methanol=15:1) using a silica gel plate of Kieselgel 60F$_{254}$ (Art. 5715). The chromatograph obtained was observed under a UV lamp at 254 nm to confirm the presence of the compounds T-23, whereupon it was confirmed that the sixteen (16) to thirtieth (30) fractions contained a pure compound T-23-I, the forthy-second (42) to fifty-third (53) fractions contained compound T-23-XI, the ninetieth (90) to hundredth and third (103) fractions contained compounds T-23-X, T-23-XII, T-23-XIII and T-23-XIV, and the hundred and tenth (110) to hundred and thirty-second (132) fractions contained a pure compound T-23-II.

The fractions containing the compounds T-23-I and T-23-II, respectively were individually distilled in vacuo to remove the solvent therefrom, thereby obtaining 1.6 g of yellow powder of compound T-23-I and 12.1 g of white powder of compound T-23-II, respectively.

The fractions containing compound T-23-XI were concentrated in vacuo to obtain 60 mg of brown powder containing compound T-23-XI. The powder thus obtained was dissolved in acetone, and the solution was subjected to silica gel thin layer chromatography (Merk's Kieselgel 60F$_{254}$ Art. 5744), developed with a mixed solvent of dichloromethane/methanol (15/1). The chromatograph obtained was observed under a UV lamp at 254 nm. Thereby, it was confirmed that compound T-23-XI fraction appeared in the vicinity of R$_f$=0.50. This T-23-XI fraction was scraped out and eluted with a mixed solvent of chloroform/methanol (10/1). The eluate was concentrated in vacuo to obtain 24 mg of white powder of compound T-23-IX. Similarly, the fractions containing compounds T-23-X, -XII, -XIII and -XIV were concentrated in vacuo to obtain 85 mg of redish brown powder.

The powder obtained was dissolved in a small amount of chloroform, and the solution was subjected to a preparative high performance liquid chromatography (Hitachi 635A Liquid Chromatograph, Detector: Nihon Bunko UVIDEC 100, Column: Kusano Kagaku C.I.G. Silica Gel Prepack Column CPS-153-1). Elution with a mixed solvent of chloroform/methanol (30/1) was carried out at a flow rate of 5 ml/min, and the eluate was detected by ultraviolet absorption at 270 nm, whereupon there appeared a peak corresponding to compound T-23-X at the retention time of 18 minutes, a peak corresponding to compound T-23-XII at the retention time of 19 minutes, a peak corresponding to compound T-23-XIII at the retention time of 21 minutes, and a peak corresponding to compound T-23-XIV at the retention time of 22 minutes. The eluates corresponding to their respective peaks were concentrated in vacuo to obtain 45 mg of compound T-23-X, 6 mg of compound T-23-XII, 2 mg of compound T-23-XIII and 8 mg of compound T-23-XIV, respectively, each as white powder.

EXAMPLE 2

The procedure as described in Example 1 was repeated to obtain fractions containing compounds T-23-X, T-23-XII, T-23-XIII and T-23-XIV, respectively. The fractions were concentrated in vacuo to obtain 85 mg of redish brown powder. This redish brown powder was subjected to fractionation treatment as mentioned below. That is, 85 mg of the powder was dissolved in acetone and the solution was subjected to a thin layer chromatography (Merk's Kieselgel 60F$_{254}$ Art. 5744) and developed with a mixed solvent of dichloromethan/methanol (15/1). The chromatograph obtained was obserbed under a UV lamp at 254 nm to confirm the presence of the T-23 substances, whereupon it was confirmed that there appeared the compound T-23-X fraction in the vicinity of R$_f$=0.32, the compound T-23-XII fraction in the vicinity of R$_f$=0.31, the compound T-23-XIII fraction in the vicinity of R$_f$=0.30, and the compound T-23-XIV fraction in the vicinity of R$_f$=0.29. The fractions corresponding to their respective compounds were scraped out, individually eluted with a mixed solvent of chloroform/methanol (10/1), and the eluated were individually concentrated in vacuo to obtain 45 mg of compound T-23-X, 6 mg of compound T-23-XI, 2 mg of compound T-23-XIII, and 8 mg of compound T-23-XIV, respectively, each as white powder.

What is claimed is:

1. A mycotrienin-related compound of the formula

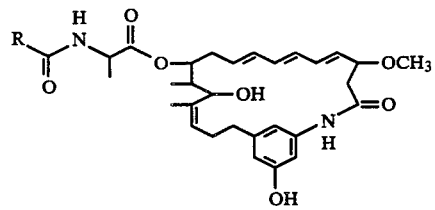

wherein R represents isobutyl, sec.-butyl, isopentyl or cyclohexyl.

2. The compound of claim 1 wherein R is cyclohexyl.
3. The compound of claim 1 wherein R is isopentyl.
4. The compound of claim 1 wherein R is sec.-butyl.
5. The compound of claim 1 wherein R is isobutyl.
6. A mycotrienin-related compound of the formula

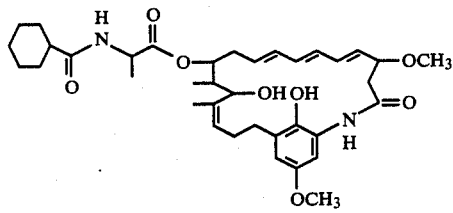

7. A method of treating tumors is a patient which comprises administering to said patient an antitumor effective amount of a compound as defined in claim 1.

8. A method according to claim 7 which comprises administering to said patient an antitumor effective amount of a compound as defined in claim 2.

9. A method of treating tumors in a patient which comprises administering to said patient an antitumor effective amount of a compound of claim 6.

10. A method according to claim 7 which comprises administering to said patient an antitumor effective amount of a compound as defined in claim 3.

11. A method according to claim 7 which comprises administering to said patient an antitumor effective amount of a compound as defined in claim 4.

12. A method according to claim 7 which comprises administering to said patient an antitumor effective amount of a compound as defined in claim 5.

* * * * *

Notice of Adverse Decisions in Interference

In Interference No. 102,551, involving Patent No. 4,649,135, N. Otake, H. Seto, T. Sasaki, N. Sugita, S. Hiramoto, MYCOTRIENIN-RELATED COMPOUNDS, final judgment adverse to the patentees was rendered Oct. 10, 1991, as to claims 7, 8 and 10-12.
*(Official Gazette December 24, 1991).*